US006810108B2

(12) United States Patent
Clark et al.

(10) Patent No.: US 6,810,108 B2
(45) Date of Patent: Oct. 26, 2004

(54) SYSTEM AND METHOD FOR POSITIONING AN ELECTRONIC PORTAL IMAGING DEVICE

(75) Inventors: Charles Clark, Pleasanton, CA (US); Loren Lentz, Pleasanton, CA (US); Debra Penny, Livermore, CA (US); William J. Gibb, San Anselmo, CA (US); Todd H. Steinberg, Antioch, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 94 days.

(21) Appl. No.: 10/214,083

(22) Filed: Aug. 6, 2002

(65) Prior Publication Data

US 2003/0086526 A1 May 8, 2003

Related U.S. Application Data

(63) Continuation-in-part of application No. 10/053,283, filed on Nov. 2, 2001.

(51) Int. Cl.$^7$ .................................................. A61N 5/10
(52) U.S. Cl. ........................................................ 378/65
(58) Field of Search ........................................... 378/65

(56) References Cited

U.S. PATENT DOCUMENTS

| | | |
|---|---|---|
| 4,995,068 A | 2/1991 | Chou et al. |
| 5,138,647 A | 8/1992 | Nguyen et al. ............. 378/189 |
| 5,233,990 A | 8/1993 | Barnea .................... 128/653.1 |
| 5,712,482 A | 1/1998 | Gaiser et al. .......... 250/363.08 |
| 5,754,622 A | 5/1998 | Hughes ........................ 378/65 |
| 5,784,431 A | 7/1998 | Kalend et al. |
| 6,282,264 B1 | 8/2001 | Smith et al. |
| 6,345,114 B1 | 2/2002 | Mackie et al. |

OTHER PUBLICATIONS

Varian, Portal Vision Brochure, Copyright Date 1999.
Clinical Use of Electronic Portal Imaging: Report of AAPM Radiation Therapy Committee Task Group 58, Michael G. Herman, et al., Medical Physics, May 2001, AIP For American Assoc. PHYS. MED, USA, vol. 28, No. 5, pp. 712–737, XP002262818, ISSN: 0094–2405, p. 732: Section V, D Advanced Applications.

*Primary Examiner*—Craig E. Church

(57) ABSTRACT

A portal imaging device positioning apparatus includes a portal imaging device positioner (255) attachable to a support (256). The portal imaging device positioner (255) is adapted to vertically adjust an imaging panel (250) in a treatment or dosimetry mode to receive radiation through a body in the patient plane (8a), and adjust the panel in a physics mode to receive radiation at the patient plane (8a).

15 Claims, 12 Drawing Sheets

SYSTEM AND METHOD FOR POSITIONING AN ELECTRONIC PORTAL IMAGING DEVICE

CROSS REFERENCE TO RELATED APPLICATIONS

The present invention is a continuation-in-part of co-pending patent application titled, SYSTEM AND METHOD FOR POSITIONING AN ELECTRONIC PORTAL IMAGING DEVICE, filed Nov. 2, 2001, Ser. No. 10/053,283. The present invention is related to co-pending U.S. patent application Ser. No. 10/053,369, titled "SYSTEM AND METHOD FOR MEASURING BEAM QUALITY AND DOSIMETRY USING ELECTRONIC PORTAL IMAGING", and which is hereby incorporated by reference in its entirety as if fully set forth herein.

BACKGROUND OF THE INVENTION

The present invention relates to a radiation emitting device, and more particularly, to a system and method for evaluating beam quality during therapy using electronic portal imaging.

DESCRIPTION OF THE RELATED ART

Radiation emitting devices are generally known and used, for instance, as radiation therapy devices for the treatment of patients. A radiation therapy device generally includes a gantry which can be swiveled around a horizontal axis of rotation in the course of a therapeutic treatment. A linear accelerator is located in the gantry for generating a high energy radiation beam for therapy. This high energy radiation beam can be an electron beam or photon (X-ray) beam. During treatment, this radiation beam is trained on one zone of a patient lying in the isocenter of the gantry rotation.

Prior to receiving therapeutic doses of radiation, the patient must be positioned accurately and precisely. Radiotherapists have historically used laser pointers and radiographic film to ensure that patients are properly positioned. This can be a complex and time-consuming process. Electronic portal imaging devices (EPIDs) can now accomplish this step much more rapidly by providing instantaneous radiographic imaging on a computer monitor. Emerging applications for EPIDs require (1) accurate and precise positioning of the EPID, (2) adequate clearance between the EPID and the patient or treatment table, and (3) maneuverability of the EPID across a sufficiently wide range of motion.

SUMMARY OF THE INVENTION

A radiation therapy apparatus according to an embodiment of the present invention includes a portal imaging device having a portal imaging device positioner for accurately positioning the EPID, providing sufficient clearance, and maneuverability across a wide range of motion.

A portal imaging device positioning apparatus according to an embodiment of the present invention includes a portal imaging device positioner attachable to a support such as a telescoping boom. The portal imaging device positioner is adapted to vertically adjust an imaging panel in either a treatment or dosimetry mode to receive radiation that has passed through a body in the patient plane, and adjust the panel in a physics mode to receive radiation at the patient plane.

The portal imaging device positioner includes an imaging panel vertically attachable to a mounting unit which in turn is vertically attachable to a main vertical drive unit. The main vertical drive unit attaches adjustably to the telescoping boom. The mounting unit includes one or more hinges for deploying the imaging panel to a horizontal position. The main vertical drive unit includes a mounting cavity on a side adjacent the telescoping boom. The main vertical drive unit is adjustable relative the telescoping boom to at least first and second positions within the mounting cavity.

A controller for the portal imaging device implements a graphical user interface that allows the position of the imaging panel to be adjusted using buttons identified with symbols to indicate the direction of motion. The interface allows positions to be stored and recalled such that the positioner moves to the desired position upon recall. Commands and sensor data are exchanged between the treatment unit and the portal imaging device controller to allow motions of the portal imaging positioner to be coordinated with other portions of the treatment unit.

In one embodiment of the present invention, the controller defines a bounding box around an X-ray field, which is then superimposed on an imaging area. If the bounding box exceeds the bounds of the imaging area, then an alarm may be provided to alert-the user, or other action may be undertaken.

BRIEF DESCRIPTION OF THE DRAWINGS

A better understanding of the present invention can be obtained when the following detailed description is considered in conjunction with the following drawings in which.

DETAILED DESCRIPTION OF THE INVENTION

Figure 1:
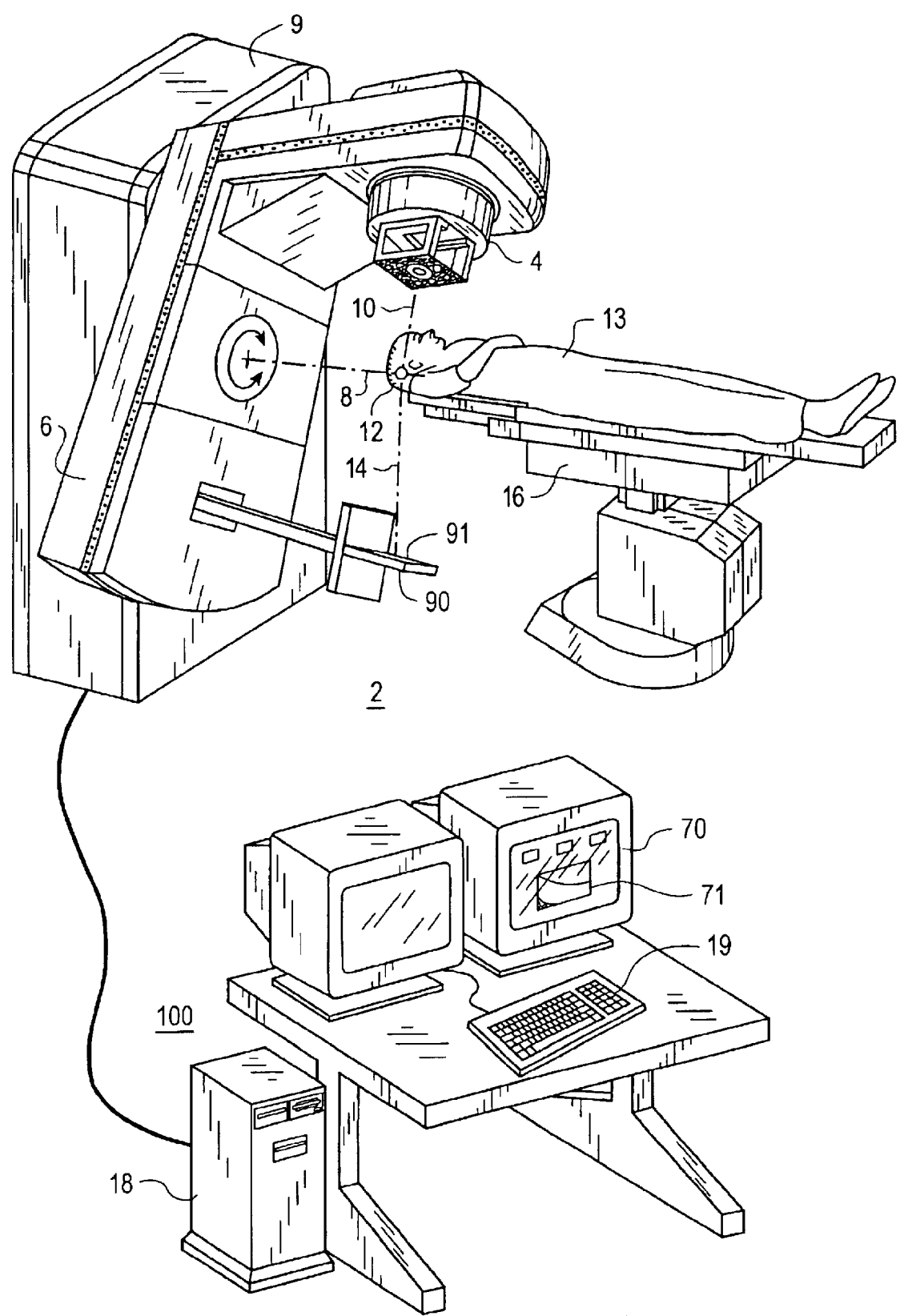
FIG. 1 is a diagram of a radiation treatment device according to an embodiment of the present invention.

Turning now to the drawings and, with particular attention to FIG. 1, a radiation treatment apparatus embodying the present invention is shown therein and generally identified by reference numeral 2. The radiation treatment apparatus 2 includes a beam shielding device (not shown) within a treatment head 4, a control unit in a housing 9 and a treatment unit 100. The radiation treatment device 2 includes a gantry 6 which can be swiveled around a horizontal axis of rotation 8 in the course of a therapeutic treatment. The treatment head 4 is fastened to projection of the gantry 6. A linear accelerator is located in the gantry 6 to generate the high powered radiation required for the therapy. The axis of the radiation beam emitted from the linear accelerator and the gantry 6 is designated by 10. Electron or photon radiation can be used for the therapy.

During the treatment, the radiation beam is trained on a zone 12 of an object 13, for example, a patient who is to be treated and who lies at the isocenter of the gantry rotation. The rotational axis 8 of the gantry 6, the rotational axis 14 of a treatment table 16, and the beam axis 10 intersect in the isocenter. Exemplary radiation treatment devices suitable for use with the teachings of the present invention are the Mevatron and Primus systems, available from Siemens Medical Systems, Inc.

A beam shielding device, such as a plurality of plates may be provided within the treatment head. Such plates are substantially impervious to the emitted radiation. The plates are mounted between the radiation source and the patient in order to delimit the field. Areas of the body, for example, healthy tissue, are therefore subject to as little radiation as possible and preferably to none at all. The plates or leaves are movable such that the distribution of radiation over the field need not be uniform (one region can be given a higher dose than another). Furthermore, the gantry can be rotated so as to allow different beam angles and radiation distributions without having to move the patient.

It is noted that plates, although common, are not the only type of beam shielding devices available. For example, many radiation therapy devices include some form of beam collimator, wedge, compensator, jaw and/or other aperture device. An aperture device itself can act as the beam shielding device and the various beam shielding devices can be combined to limit the delivered radiation. The present invention can be used with any such arrangement and can also be used in dynamic conformal treatments in which the gantry, collimator, jaws and multileaf collimators could all be in motion during the radiation delivery.

The radiation treatment device 2 also includes a central treatment unit 100 which is typically located apart from the radiation treatment device 2. The radiation treatment device 2 is normally located in a different room to protect the therapist from radiation. The treatment unit 100 includes output devices such as at least one visual display unit or monitor 70 and an input device such as a keyboard 19. Data can be input also through data carriers such as data storage devices or a verification and recording or automatic setup system. Thus, display area 71 can cover a portion of the screen and can be designed as a window or as an icon. In addition to the measured delivered radiation, the prescribed radiation can also be shown on the screen. The display of the measured delivered radiation may be carried out in real time. Thus, at any time during treatment, the amount of delivered radiation can be verified. In addition, at the end of a treatment, the overall delivered radiation can be verified with the prescribed radiation. This can be initiated automatically with a software program capable of detecting the end of a treatment, or this can be initiated manually by, for example, a therapist. Instead of or in addition to monitor 70, other output devices, such as a printer, can be utilized.

The treatment processing unit 100 is typically operated by the therapist who administers actual delivery of radiation treatment as prescribed by an oncologist by using the keyboard 19 or other input device. The therapist enters into the control unit of the treatment unit 100 the data that defines the radiation dose to be delivered to the patient, for example, according to the prescription of the oncologist. The program can also be input via another input device, such as a data storage device. Various data can be displayed before and during the treatment on the screen of the monitor 70.

In addition, a portal imaging system 90 may be attached to the gantry 6. Because the portal imaging system 90 is mounted on the gantry 6, portal images can be obtained at any gantry angle and during rotation of the gantry 6. The portal imaging system may include a flat panel, amorphous silicon detector implemented as one or more arrays of photo-sensors.

The portal imaging system includes a detector unit 91 capable of measuring the radiation exiting the object 13. The amount of radiation exiting object 13 can be used to verify the radiation treatment in a treatment mode. Thus, the detector unit 91 is used to gather the patient's exit dose information. The radiation dose is then reverse calculated by the CPU 18. The delivered radiation dose is then compared to the planned delivery dose. If these dose amounts match, the prescription was executed as planned. If the amounts do not match, measures can be taken for correction.

In addition, the portal imaging system allows characterization of all beams produced by the linac in a characterization or physics mode. The beam data includes relative beam profiles and absolute dosimetric quantities with varying machine conditions (fields sizes, energies, beam modifiers, dose rates, setup conditions, etc.). Once the data has been collected, it is used to set up dosimetry tables and to commission the treatment planning computer used for dose calculations.

Figure 2:
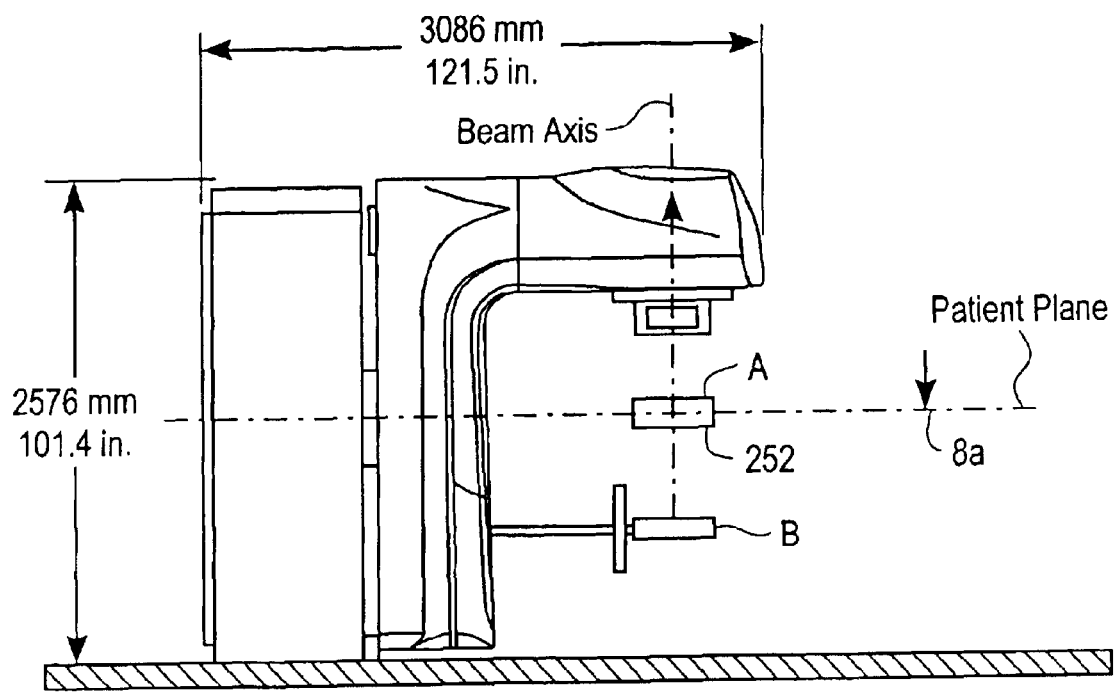
FIG. 2 is a diagram illustrating the adjustability of a portal imaging device positioner according to an embodiment of the present invention.

To properly commission the medical linac, data must be collected under normal clinical conditions of the machine. This data must be collected at various depths with respect to the isocentric plane. A portal imaging system according to embodiments of the present invention allows both commissioning the linac and measurement of patient exit dosimetry. More particularly, as will be explained in greater detail below, the portal imaging device platform 252 is adjustable in a vertical direction and, as such, is usable for both device commissioning and patient dosimetry. That is, as shown in FIG. 2, the portal imaging device platform 252 is adjustable in a position A in the patient plane 8a, for use in commissioning the machine, and in a position B for use in dosimetry. The treatment unit 100 may be used for controlling deployment of the portal imaging system from one mode to the other. In addition, as will be explained in greater detail below, the user interface is provided in conjunction with the portal imaging device and the treatment unit to control the deployment of the imaging device platform.

Figure 3A:
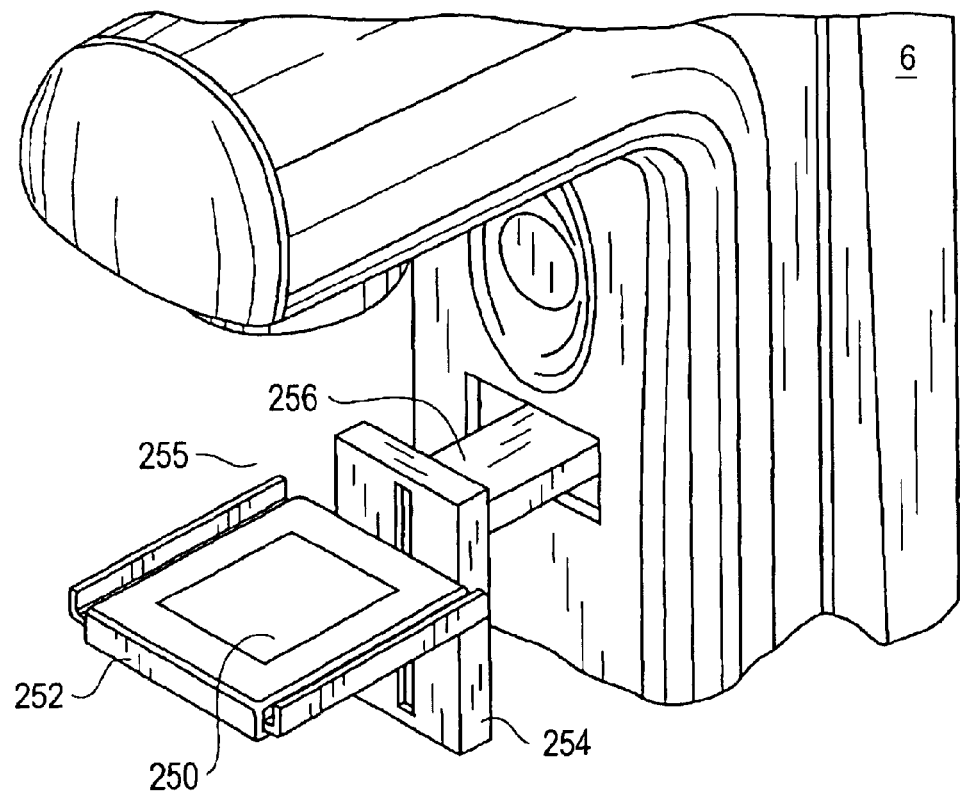
FIG. 3A and FIG. 3B illustrate a portal imaging device positioner according to an embodiment of the present invention.

Turning now to FIG. 3A, a diagram of a portal imaging device positioner according to an embodiment of the present invention is shown. The portal imaging device positioner 255 includes a platform 252 which may be embodied as a collision bumper to protect against injury or damage. Underneath the collision bumper 252 is the EPID panel 250. The collision bumper 252 and EPID panel 250 ride vertically on the vertical drive unit or backplane 254. The backplane 254 itself can be moved in and out from the gantry. These movements are all motorized and can be controlled manually or automatically by the treatment control system 100.

Figure 3B:
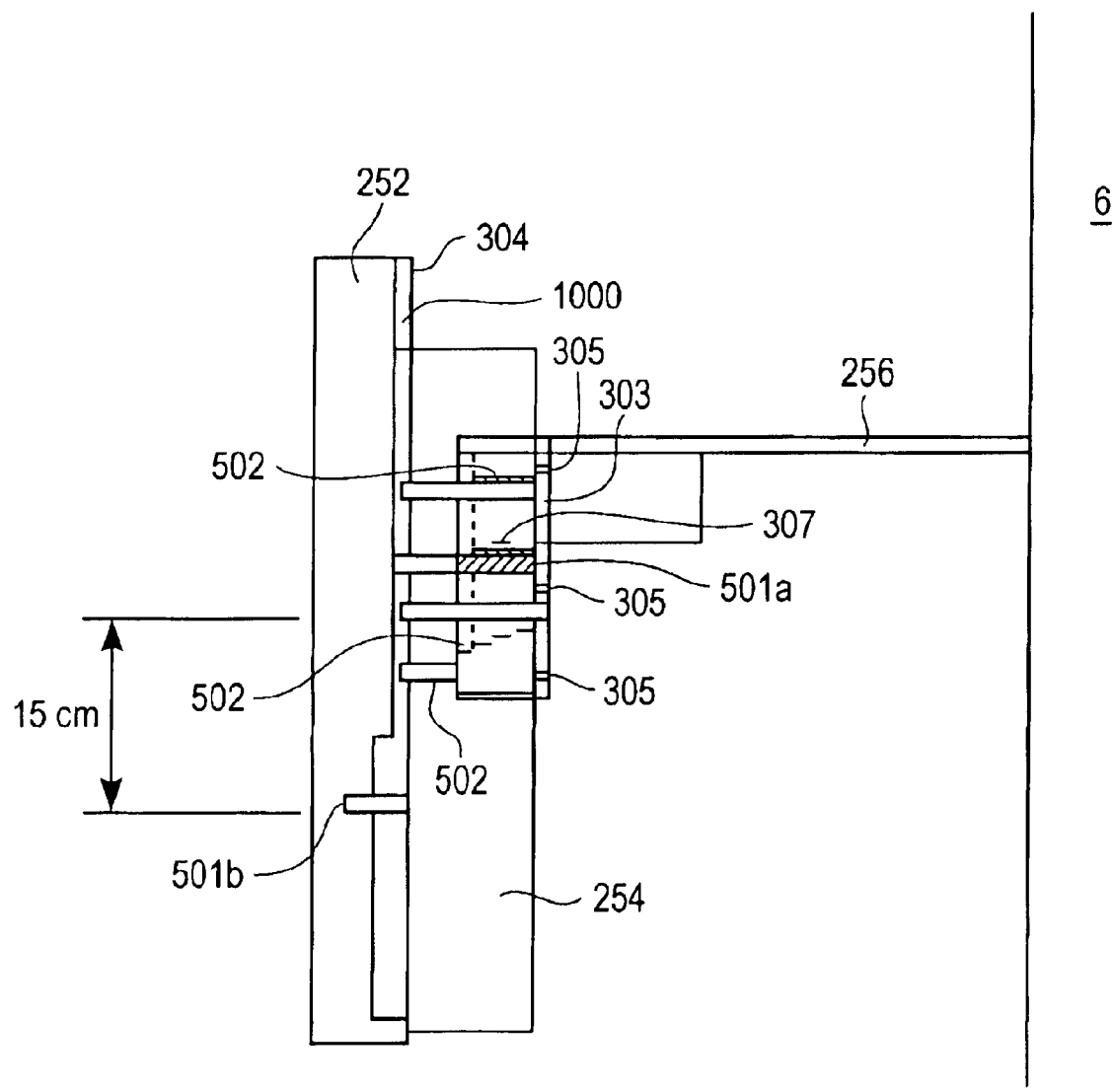

FIG. 3B illustrates various components of the portal imaging device positioner in a schematic view. As shown, the portal imaging device positioner attaches to the gantry 6 by a support such as a telescoping boom 256. A computer-controlled motor within the gantry 6 (not shown) may be used to extend and retract the portal imaging device positioner. The imaging platform 252 mounts to the vertical drive unit 254 via the mounting unit 1000. The platform 252 is extendable into a horizontal position using one or more hinges 304. The extension into horizontal position may be accomplished using a computer-controlled motor (not shown).

In the embodiment illustrated, the vertical drive assembly 254 includes a mounting cavity 307 to allow for vertical movement of the platform 252 with respect to the telescoping boom 256. In a treatment mode, the top of the telescoping boom 256 is generally aligned with the top of the mounting cavity 307. In a physics mode, the bottom of the telescoping boom 256 is generally aligned with the bottom of the mounting cavity 307. A plurality of bolt holes 502 may be provided in the vertical drive assembly 254 to allow bolts to affix the vertical drive assembly 254 to the telescoping boom 256. Holes 501a, 501b may also be provided, to allow insertion of a "physics pin" to secure the platform 252 to the telescoping boom 256, as will be explained in greater detail below. Finally, a protective panel 303 may cover the mounting cavity 307 and may include a plurality of screw holes 305 for securing it in place.

Initially, in operation, the portal imaging device positioner is configured in a treatment mode. In this mode, the positioner is in place below the patient plane and the platform 252 can be deployed to receive radiation that passes through the patient. The top of the telescoping boom 256 is positioned substantially adjacent the top of the mounting cavity 307.

To change to the physics mode, the platform 252 is raised with respect to the vertical drive assembly 254 and telescoping boom 256. In one embodiment, the platform 252 is raised about 15 centimeters, so that the physics pin hole portions 501a, 501b are aligned.

The protective cover 303 is then removed, to allow installation of a physics pin into the physics hole. Bolts are then removed from the bolt holes 502 to allow movement of the vertical drive assembly 254 with respect to the telescoping boom 256. The main vertical drive assembly 254 is then raised relative to the telescoping boom 256. In particular, in one embodiment, the main vertical drive assembly 254 is raised 15 centimeters, such that the bottom of the telescoping boom 256 is substantially adjacent the bottom of the mounting cavity 307. The bolts are then replaced, the physics pin is removed, and the panel can be deployed.

Adjustment of the portal imaging device positioner from treatment mode to physics mode is illustrated in greater detail with reference to FIGS. 4–9.

Figure 4:
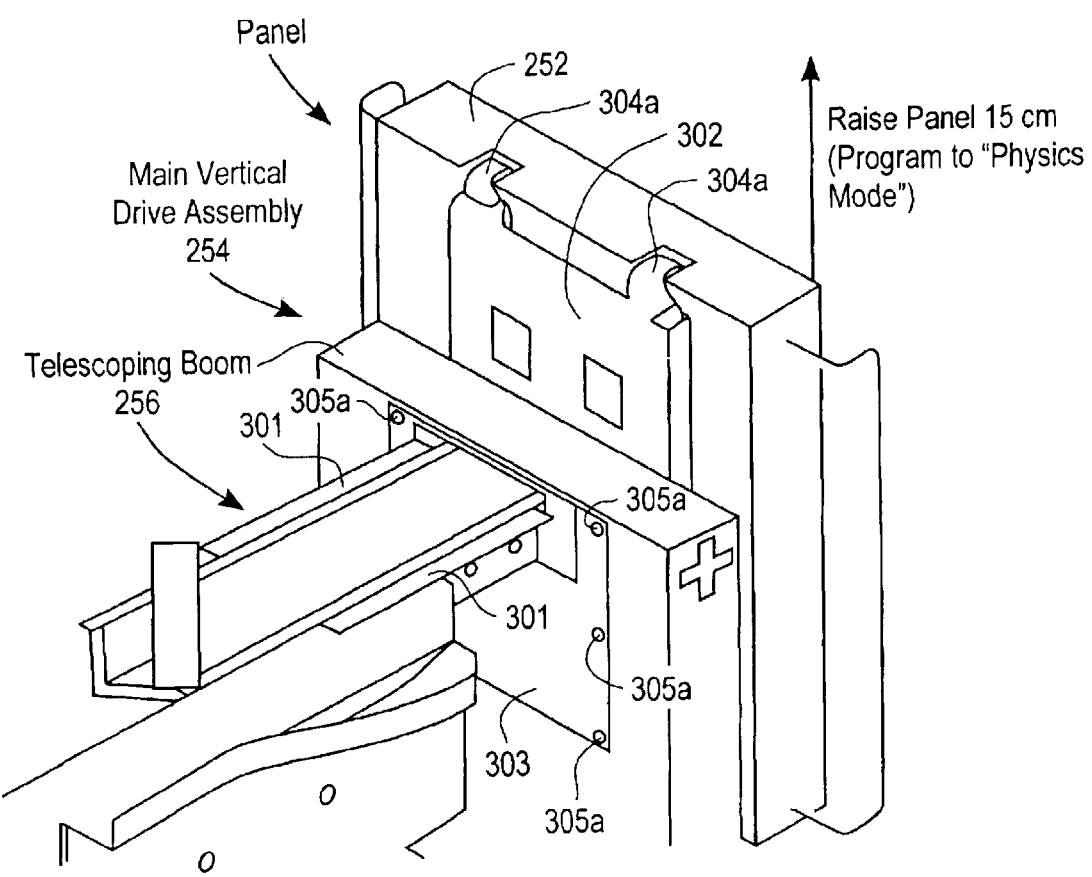
FIG. 4 is a diagram illustrating adjustment of a portal imaging device positioner according to an embodiment of the present invention.

As shown in FIG. 4, the main vertical drive assembly 254 is fixed to the telescoping boom 256 via one or more brackets 301 and a plate 303. The platform 252 attaches vertically to the main vertical drive assembly 254 via one or more hinges 304a, 304b. In operation, the platform 252 swings out horizontally on the hinges 304a, 304b, to receive radiation during both modes of operation. The platform 252 is typically stored vertically to save space. In addition, the plate 303 attaches to the main vertical drive assembly 254 via a plurality of fasteners, such as screws 305A, which fit into screw holes 305 (FIG. 3B). In on embodiment six (6) screws are provided (two of which are obscured in the figure by the telescoping boom 256).

To change the mode of operation from the treatment mode to the physics mode, the vertical drive assembly 254 is adjusted such that the platform 252 can be fixed in a higher position, i.e., in the patient plane. Initially, the platform 252 is raised from a default position to the physics position in the direction of the arrow 306. In one embodiment of the present invention, the platform 252 is raised about 15 centimeters.

Figure 5:
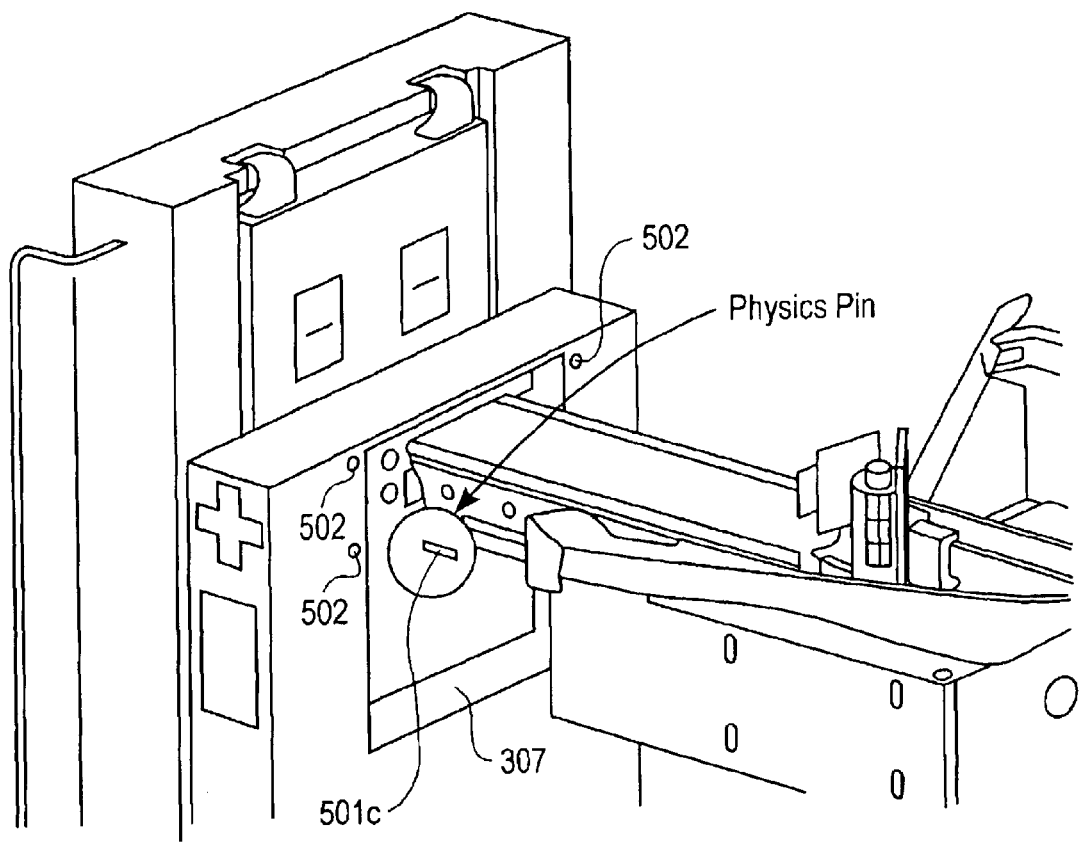
FIG. 5 is a diagram illustrating adjustment of a portal imaging device positioner according to an embodiment of the present invention.

The physics cover 303 is then removed by removing the screws 305A. As will be explained in greater detail below, this allows access to the mounting cavity 307. More particularly, as shown in FIG. 5, a "physics pin" 501c may be installed, to secure the platform 252 to the telescoping boom 256. In addition, bolts 502A that secure the vertical positioner to the telescoping arm are removed. In on embodiment of the invention, four such bolts are provided, only three of which are visible in the figure.

Figure 6:
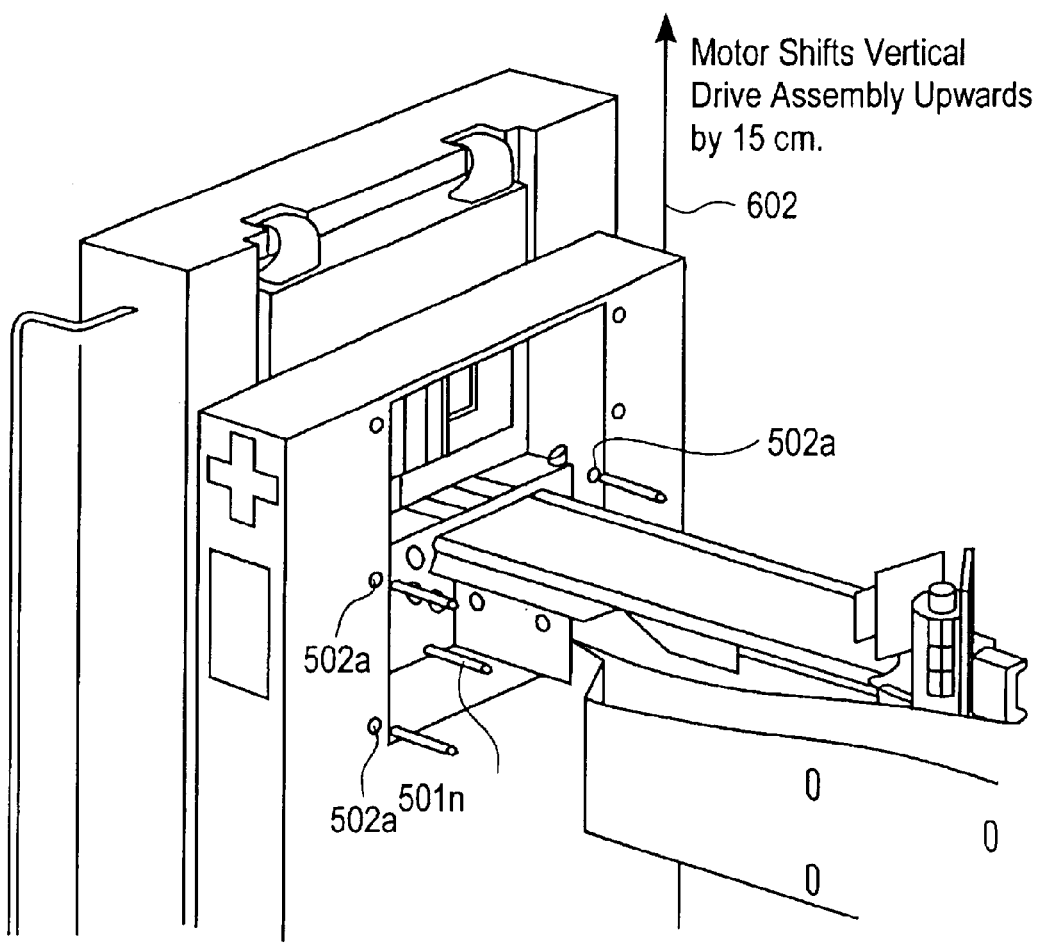
FIG. 6 is a diagram illustrating adjustment of a portal imaging device positioner according to an embodiment of the present invention.
Figure 7:
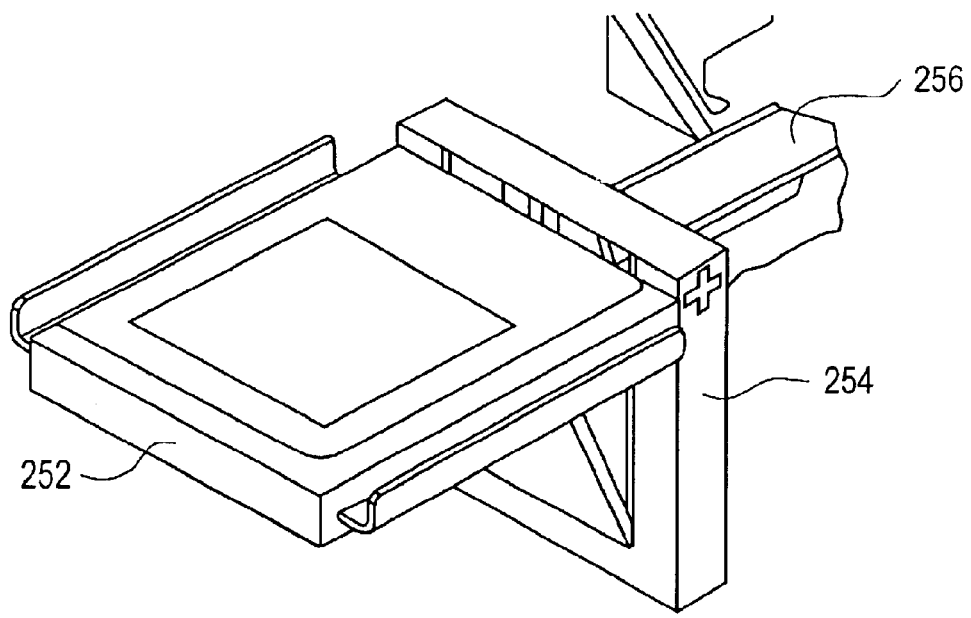
FIG. 7 is a diagram illustrating adjustment of a portal imaging device positioner according to an embodiment of the present invention.

As shown in FIG. 6, removal of the bolts 502A allows the vertical drive assembly to move in the direction of the arrow 602. The presence of the physics pin 501A means that the platform 252 is affixed to the telescoping arm. Thus, the vertical drive assembly 254 moves relative to both. Next, the bolts 502A are replaced and the physics pin 501A is removed. This fixes the vertical drive assembly 254 to the telescoping boom 256 in the physics position. Next, as shown in FIG. 7, the platform 252 may be deployed in a standby position by extending the panel along the hinges 304a, 304b.

Figure 8:
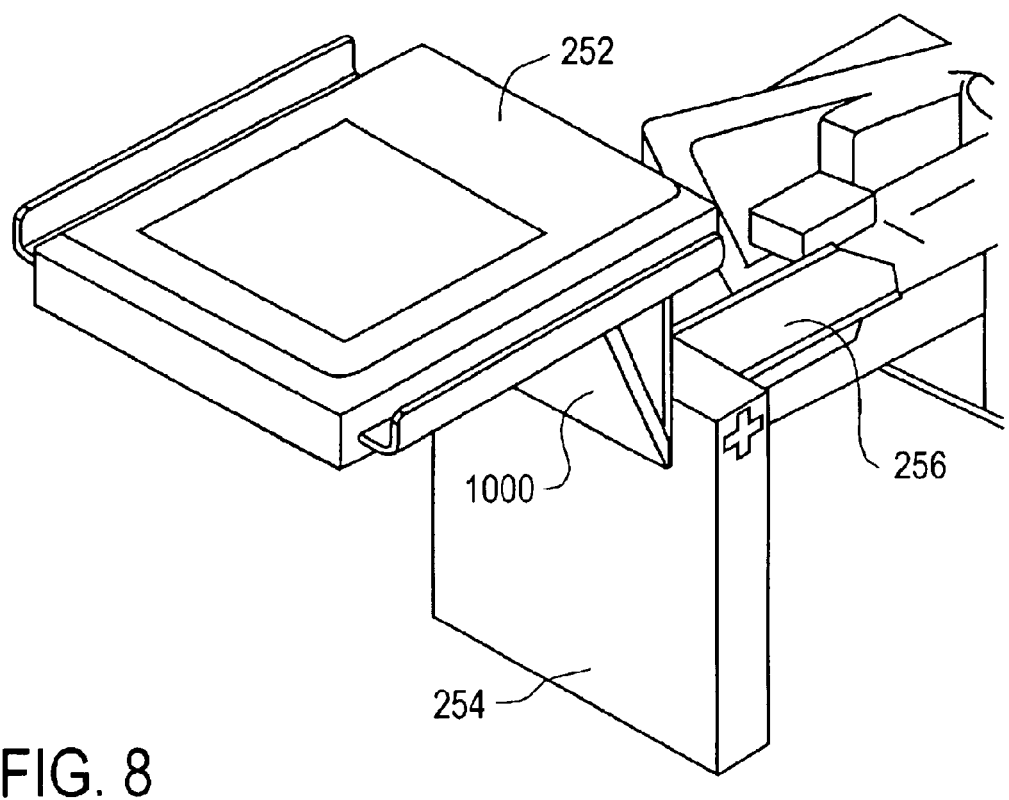
FIG. 8 is a diagram illustrating adjustment of a portal imaging device positioner according to an embodiment of the present invention.
Figure 9:
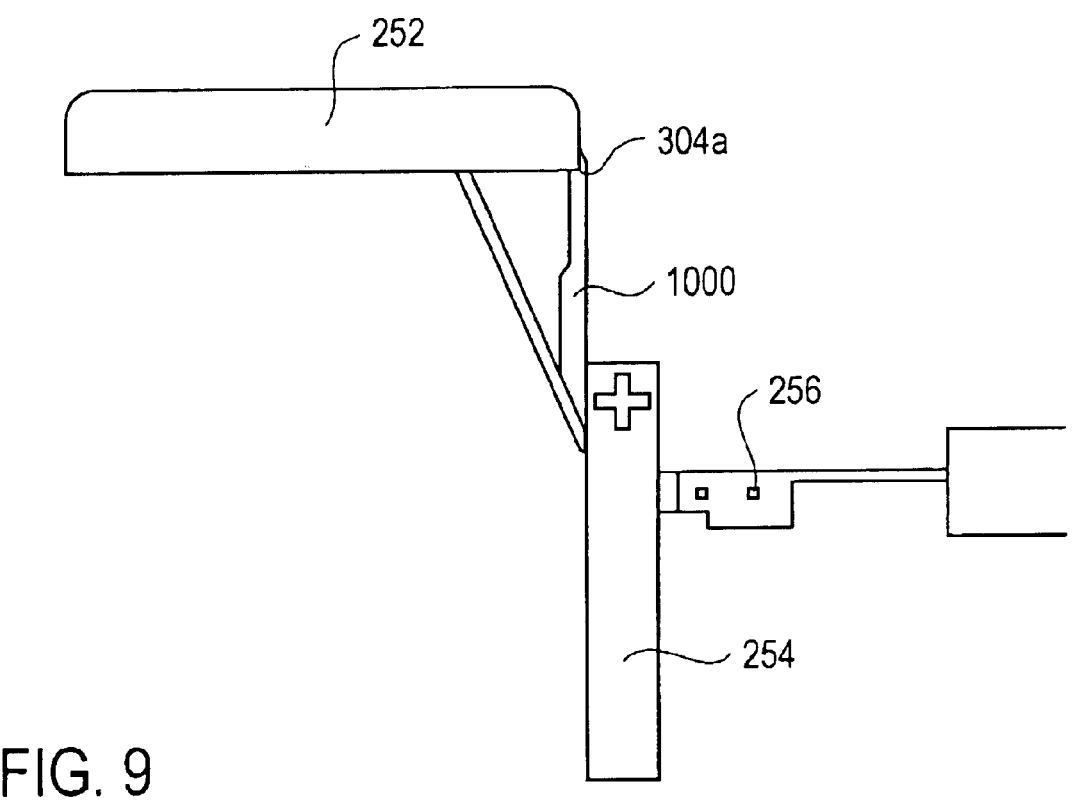
FIG. 9 is a diagram illustrating adjustment of a portal imaging device positioner according to an embodiment of the present invention.

Finally, the panel is deployed in the physics position, as shown in FIGS. 8 and 9. As shown, the portal imaging system includes the deployed horizontal platform 252, extended on the hinges 304a, b.

It is noted that a variety of mechanisms could be employed to position the imaging panel at the patient plane and in the dosimetry position. These include, for example, direct lift systems that do not employ the mounting cavity system described above. Thus, for example, in certain embodiments, the lifting of the platform 252 itself is sufficient to position the panel from the patient dosimetry position to the patient plane. Furthermore, in other embodiments, the platform 252 may be stored horizontally.

As noted above, a graphical user interface on the treatment console 100 may be used to control deployment of the portal imaging device and its platform 252. A controller associated with the graphical user interface (e.g., implemented by CPU 18) also provides an interface between gantry control and portal imaging device control. In addition, the controller may implement a "bounding box" to ensure that the incident field remains within the active imaging area.

Figure 10:
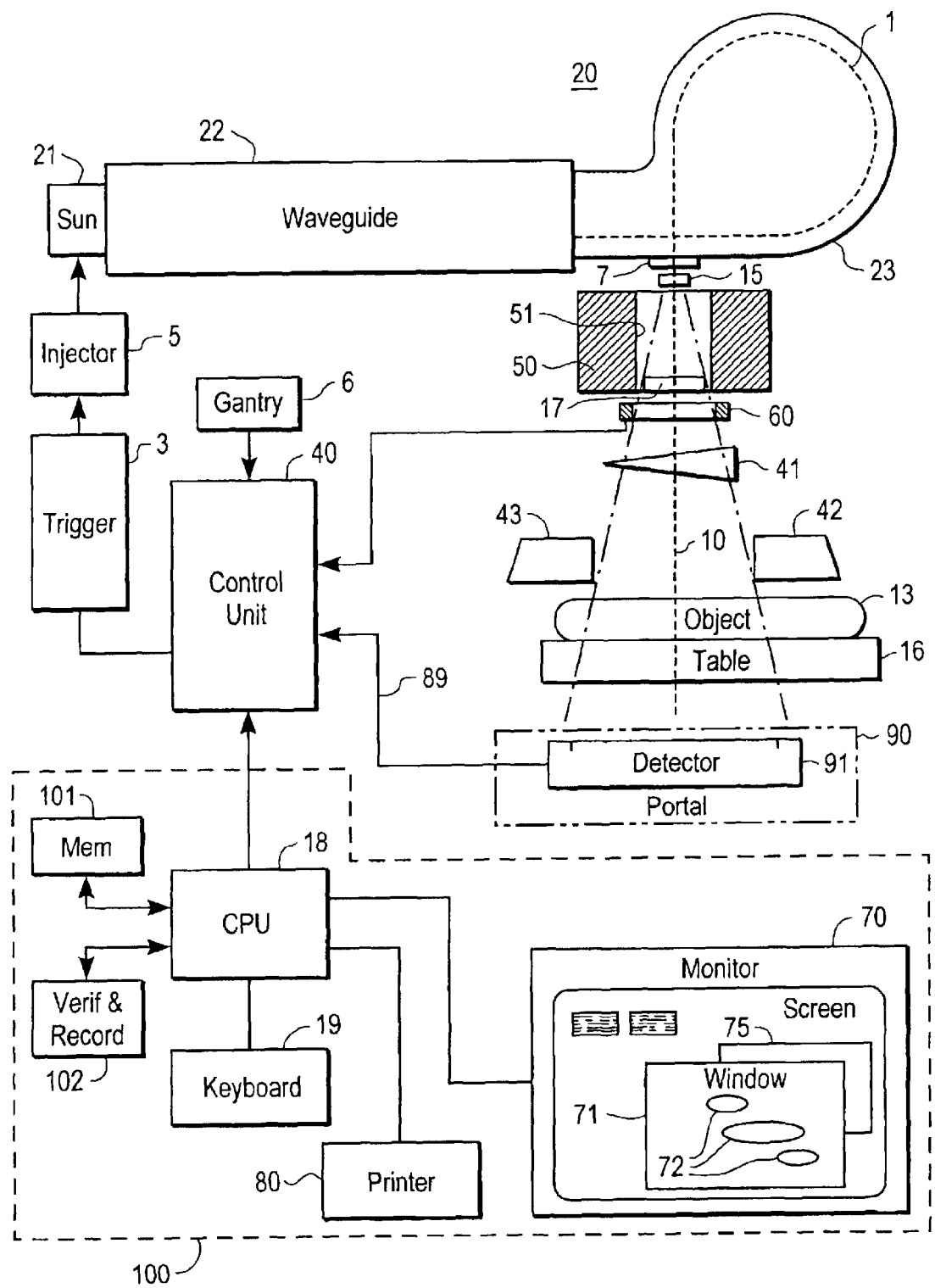
FIG. 10 is a diagram illustrating portions of a processing unit, a control unit, and a beam generation unit for the radiation treatment device of FIG. 1.

More particularly, FIG. 10 shows portions of radiation treatment device 2 and portions of treatment unit 100 in more detail. An electron beam 1 (also referred to as a radiation beam) is generated in an electron accelerator 20. Accelerator 20 includes an electron gun 21, a wave guide 22 and an evacuated envelope or guide magnet 23. A trigger system 3 generates injector trigger signals ad supplies them to injector 5. Based on these injector trigger signals, injector 5 generates injector pulses which are fed to electron gun 21 in the accelerator 20 for generating the electron beam 1. The electron beam 1 is accelerated and guided by wave guide 22.

For this purpose, a high frequency (HF) source is provided which supplies radio frequency (RF) signals for the generation of an electromagnetic field supplied to wave guide 22. The electrons injected by injector 5 and emitted by electron gun 21 are accelerated by this electromagnetic field in wave guide 22 and exit at the end opposite to electron gun 21 as electron beam 1. Electron beam 1 then enters guide magnet 23, and from there is guided through a window 7 along axis 10. After passing through a first scattering foil 15, the beam goes through a passageway 51 of a shield block 50 and encounters a second scattering foil 17. Next, it is sent through a measuring chamber 60, in which the radiation dose is ascertained. If the radiation beam is an x-ray beam, the scattering foils are replaced by a target. A wedge filter 41 and aperture plates 42 and 43 can be provided in the path of radiation beam 1 such that the radiation is focused on the area to be irradiated. As noted above, this is just one example of a beam-shielding arrangement that can be used in the present invention.

As stated above, a detector unit 91 is arranged beneath object 13 from the viewpoint of the beam source. In one embodiment, detector unit 91 is located within portal imaging system 90. The amount of the radiation beam delivered to object 13 is measured by detector unit 91 such that radiation is sensed after it has passed through object 13.

FIG. 10 also shows various portions of the treatment unit 100. Monitor 70 and keyboard 19 are connected to CPU 18. A printer 80 can also be provided to record information related to the treatment. CPU 18 is programmed to assist in the control of radiation treatment device 2. According to the instructions of the oncologist, the therapist programs CPU 18, so that it carries out the prescribed course(s) of radiation treatment. In window 71 on the screen of monitor 70, curves 72 indicate the prescribed delivery of the radiation treatment. In addition, other windows implementing a graphical user interface 73 can be used to set the mode and function of the portal imaging device 90. More particularly, as will be explained in greater detail below, graphical icons can be used to control the positioning of the panel 252. A memory 101 along with a verification and recording system 102 can be connected to CPU 18.

A control unit 40 receives position information from gantry 6, and it receives information about radiation emission from measuring chamber 60. Detector unit 91 provides exit radiation signals 89 to control unit 40. These exit radiation signals 89 include information about the amount of radiation which has passed through object 13. CPU 18 processes signals received from control unit 40 and reverse calculates the incident beam for the distributed radiation. In one embodiment, this incident beam is based on exit radiation signals 89 and on attenuation factors (e.g., the anatomical attenuation factors of object 13). The incident beam can also be based on exit radiation signals 92 alone. CPU 18 can then output a two dimensional or a three dimensional display of a radiation delivered dose map. This radiation map can be in the form of radiation dose curves 72 which provide a three dimensional display. The radiation map displays the measured amount of radiation which has been distributed through object 13. Additionally, control icons and other curves, such as curves representing the planning system dose and/or icons related to a wedge function, can also be displayed on monitor 70.

In addition, the control unit 40 receives position information from the portal imaging device 90. This allows the motion of the gantry and other portions of the treatment device to be coordinated with the movements of the portal imaging device. Further, the treatment unit 100 receives the portal imaging device position information which allows the treatment unit 100 to control operation of the portal imaging device in conjunction with the treatment device and also display status and motions of both on screen 70.

Figure 11:
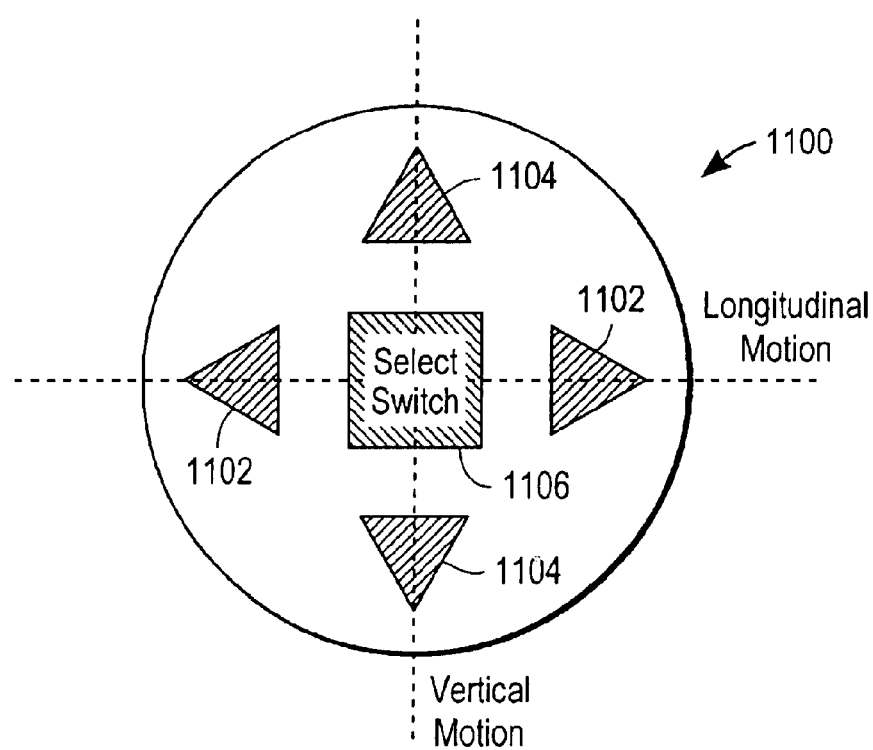
FIG. 11, FIG. 12, and FIG. 13 illustrate exemplary user interfaces for controlling a portal imaging device according to an embodiment of the present invention.

Turning now to FIG. 11, a diagram of a direction and speed control according to an embodiment of the present invention is shown. More particularly, shown is a control interface 1100 including longitudinal motion controls 1102, vertical motion controls 1104, and a speed control 1106. The control interface 1100 may be embodied as a graphical user interface displayable on screen 70 and activatable via keyboard or cursor device, such as a mouse, and implemented by CPU 18. Alternatively, the control interface 1100 may be implemented as a separate, computer-connectable peripheral device.

The speed control 1106 allows the user to set a speed for maneuvering and deploying the imaging platform. In certain embodiments, for example, selecting the speed control 1106 allows the user to set a speed from a range of speeds. Thus, for example, clicking on the control 1106 may cause another pop up window to be displayed, which provides a range from which the user can select the speed. In other embodiments, the control 1106 is merely a mode control, allowing the user to select "fast" or "slow."

Once the speed has been selected or pre-set, the user can maneuver the imaging platform using the directional controls 1102, 1104. As can be appreciated, the longitudinal controls allow the user to position the imaging platform vertically (i.e., in the y-direction), and the longitudinal controls 1104 allow the user to position the imaging platform in the x-direction.

Figure 12:
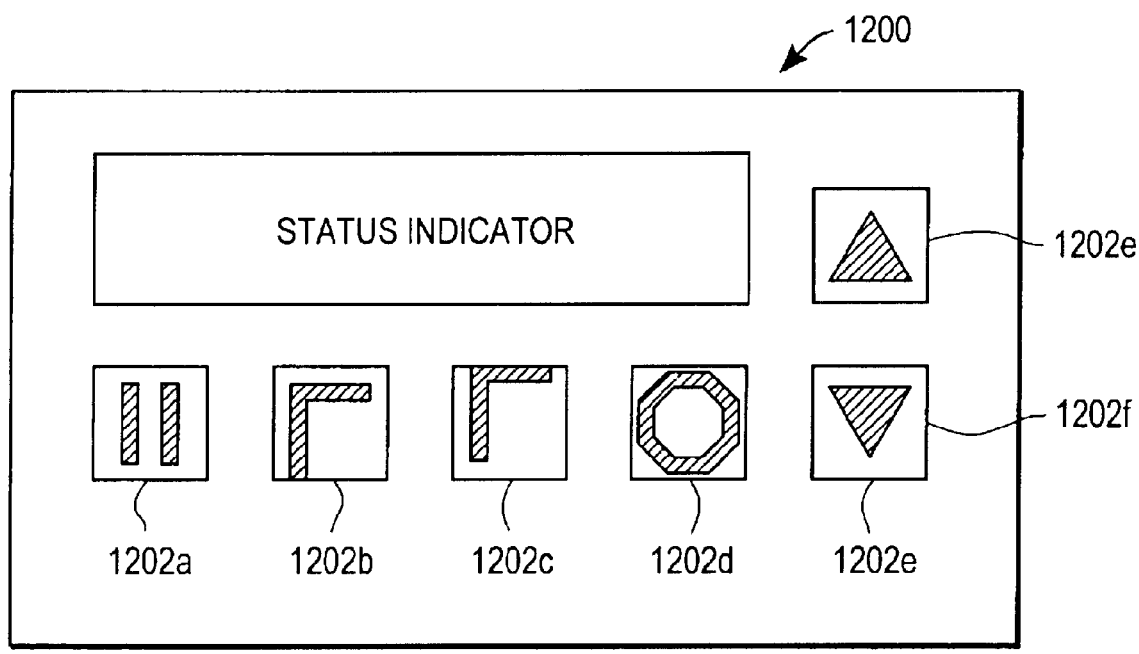

FIG. 12 illustrates another control panel 1200, which likewise may be provided as a graphical user interface in window 73. The control 1200 includes a plurality of function keys 1202a–1202f. The function keys shown allow particular portal imaging device operation at the touch of the key. Thus, selection of key 1202a retracts the positioner to the parked position; selection of key 1202b deploys the positioner to the standby position; selection of the key 1202c deploys the positioner to the mid-field position; and selection of the key 1202d stops the positioner. The function keys 1202e, 1202f allow the user to store a position of the positioner and recall the positioner to that position.

Figure 13:
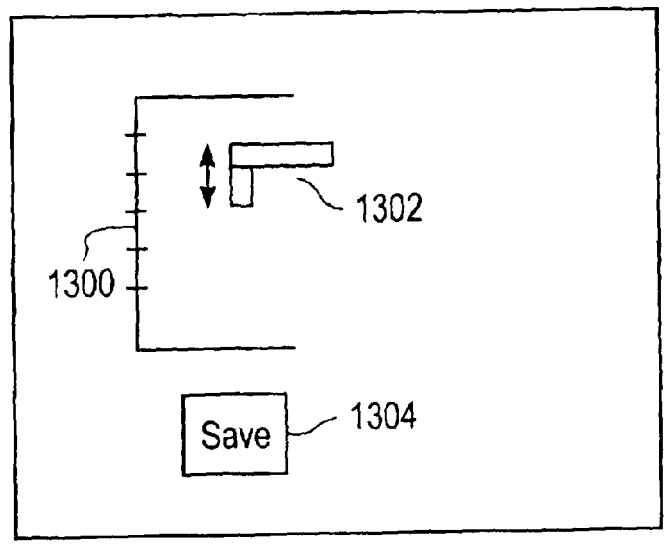

For example, shown in FIG. 13 is an exemplary interface for setting a portal imaging device position according to an embodiment of the present invention. The interface 1300 includes a position graph 1300 and a positioner icon 1302. Also, a SAVE key 1304 is provided. In operation, the user may click or double click one of the programmable keys 1202e, 1202f (FIG. 12) and navigate to the screen of FIG. 13. The user can then move the icon 1302 to a desired position, referenced with respect to the graph 1300. Once the user has set the position of the icon 1302, the position can be saved by clicking the save button 1304. Subsequently, the user can automatically position the portal imaging device as set by clicking the button 1202e.

Figure 14A:
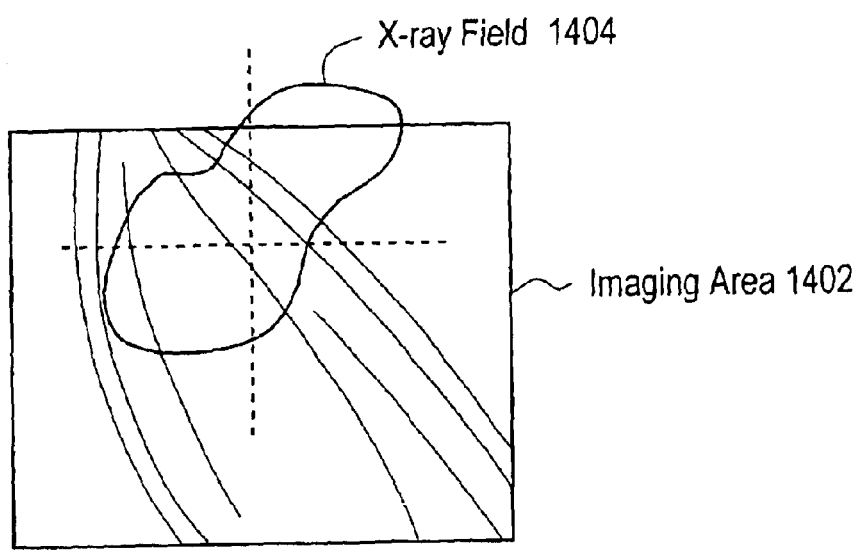
FIGS. 14A–14D illustrate edge sensing according to an embodiment of the present invention.

As noted above, one aspect of the present invention relates to ensuring correct delivery of the radiation dose and imaging. In particular, shown in FIG. 14A are an active imaging area 1402 and a two-dimensional cross section of an X-ray field 1404 projected onto the imaging area 1402. To avoid potential damage to electronics (not shown) situated around the perimeter of the active imaging area 1402, it is desired to detect cases in which the X-ray field exceeds the bounds of the active imaging area 1402

Figure 14B:
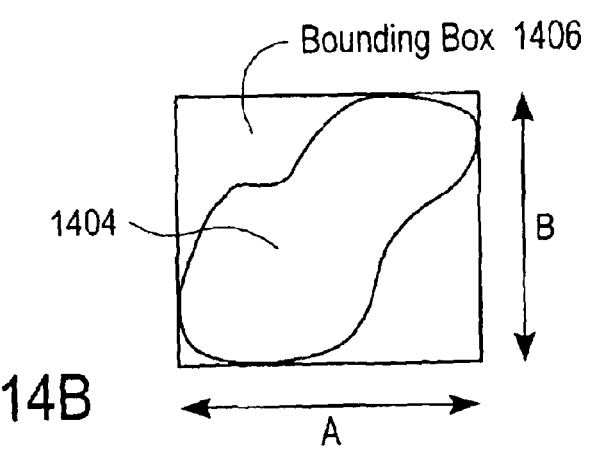
Figure 14C:
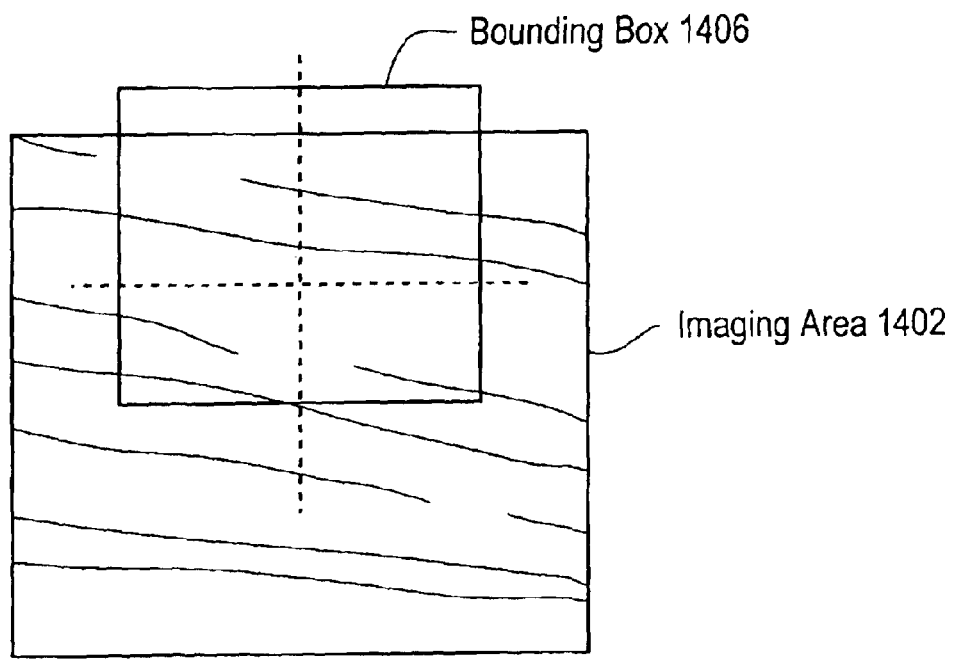
Figure 14D:
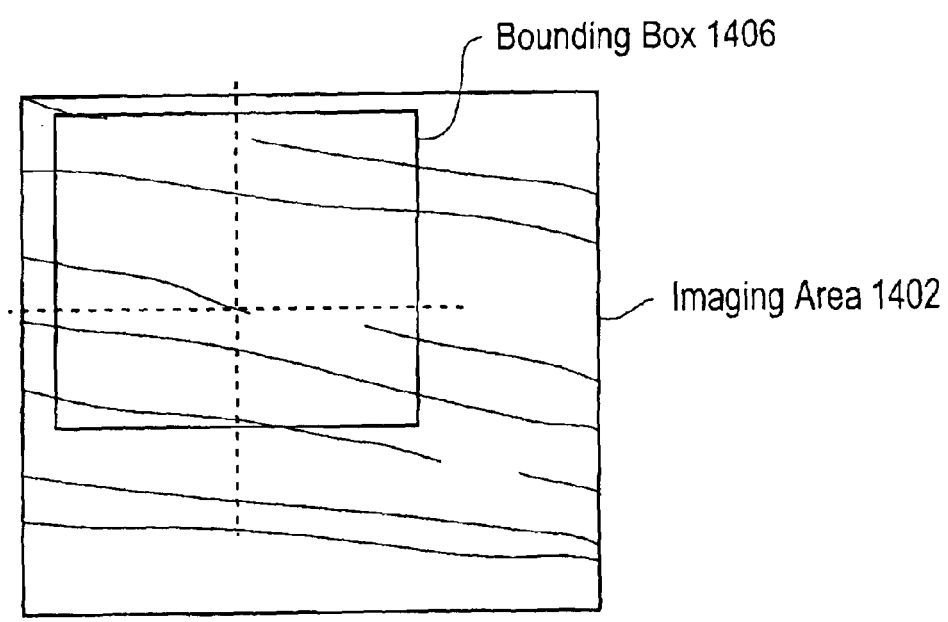

To prevent this from occurring, according to embodiments of the present invention, the treatment unit computes a bounding box around the X-ray field, as shown in FIG. 14B. The bounding box 1406 has dimensions A and B that define the maximum bounds of the X-ray field. The bounding box 1406 is then superimposed by the treatment unit 18 on the imaging area 1402, as shown in FIG. 14C. If the bounding box 1406 exceeds the bounds of the active imaging area 1402, then the treatment unit may issue a warning to the therapist. Alternatively, the treatment unit may cause the system to shut down or cease applying the X-ray field. However, as shown in FIG. 14D, if the bounding box 1406 is completely within the bounds of the imaging area 1402, then the treatment will proceed. In addition, the two-dimensional image of the X-ray field, bounding box, and active imaging area may be displayed on the graphical user interface.

Figure 15A:
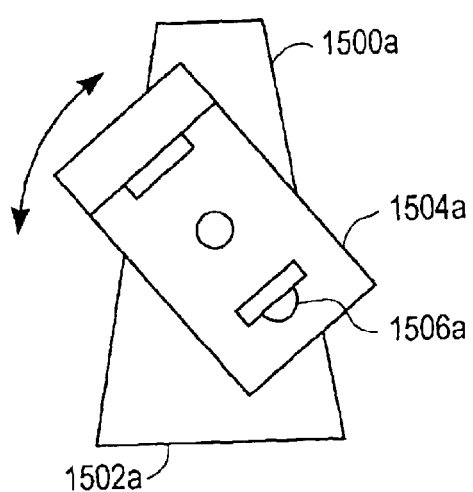
FIG. 15A–FIG. 15D illustrate exemplary graphical user interfaces for a radiation therapy device according to an embodiment of the present invention.
Figure 15B:
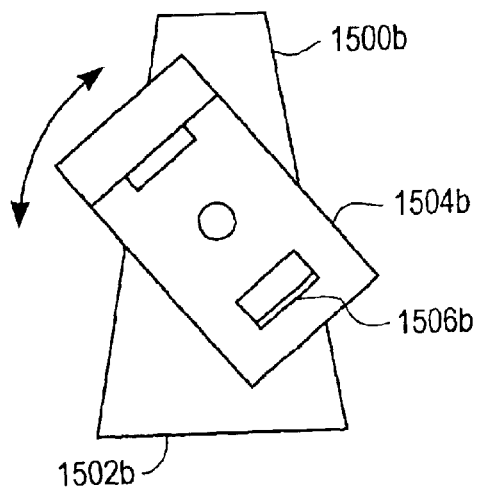

FIG. 15A–FIG. 15D illustrate exemplary user interface icons or graphics representative of various positions for the gantry and portal imaging device. Shown in FIG. 15A is an exemplary graphic 1500a. The graphic 1500a is representative of a position of the radiation therapy device, including stand 1502a, gantry 1504a, and portal imaging device 1506a. As shown the gantry 1504a can pivot in the direction of the arrow and is shown pivoted from the vertical. Also, the portal imaging device may be shown in various stages of deployment. As shown in FIG. 15A, the portal imaging device is shown as being deployed, for example. Similarly, FIG. 15B illustrates graphic 1500b, along with stand 1502b, gantry 1504b, and portal imaging device 1506b. However, in FIG. 15B, the portal imaging device 1506b is shown in a different position, such as a retracted position.

Figure 15C:
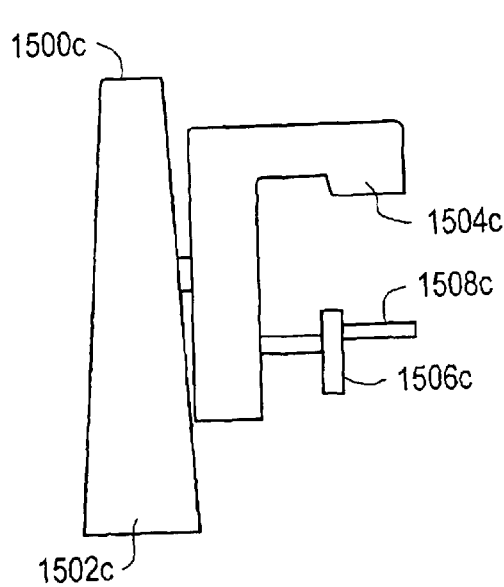
Figure 15D:
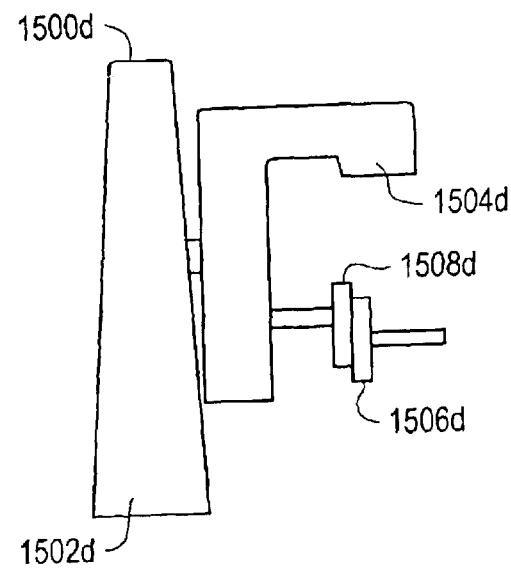

As can be appreciated, the radiation therapy device and associated portal imaging device can be displayed in other views and/or configurations. Thus, for example, FIG. 15C illustrates device 1500c, along with stand 1502c, gantry 1504c, and portal imaging device 1506c. The portal imaging device 1506c is shown in a deployed position with the platform 1508c in the patient plane. Finally, FIG. 15D shows the device 1500d with the portal imaging device in the retracted position 1508d. It is noted that the graphical user interface of embodiments of the present invention can be used to show more or fewer views, as desired. Thus, the figures are exemplary only.

Thus, the invention described in the above detailed description is not intended to be limited to the specific form set forth herein, but is intended to cover such alternatives, modifications and equivalents as can reasonably be included within the spirit and scope of the appended claims.

What is claimed is:

1. A portal imaging device positioning apparatus attachable to a radiation therapy device gantry, comprising:
   a support attachable to said gantry;
   a vertically-adjustable portal imaging device positioner attachable to said support, said portal imaging device positioner operable in a first mode and a second mode, wherein in said first mode said portal imaging device positioner maintains an imaging panel in position to receive radiation passing through a body maintained in a patient plane, and wherein in said second mode portal imaging device positioner maintains said imaging panel to receive radiation substantially at said patient plane; and
   a graphical user interface adapted to control deployment of said portal imaging device positioner.

2. A portal imaging device positioning apparatus according to claim 1, said graphical user interface adapted to display movements of said portal imaging device positioner and said gantry.

3. A portal imaging device positioning apparatus according to claim 2, further including a controller adapted to define a boundary for an radiation field and determine if an extent of said boundary exceeds an extent of a boundary of an imaging area.

4. A portal imaging device positioning apparatus according to claim 1, said graphical user interface adapted to allow a user to adjust a position of the imaging panel using buttons with symbols labeled to indicate a direction of motion.

5. A portal imaging device positioning apparatus according to claim 4, said graphical user interface adapted to store multiple configurations of said imaging panel and automatically move the imaging panel to the stored configuration.

6. A radiation therapy device, comprising:
   a linear accelerator for providing radiation to a body; and
   an electronic portal imaging device operably coupled to said linear accelerator; and
   a control unit including a user interface and adapted to control deployment of an imaging panel of said electronic portal imaging device from a substantially vertical position to a substantially horizontal position.

7. A radiation therapy device according to claim 6, said user interface adapted to allow a user to adjust a position of the imaging panel using buttons labeled with symbols to indicate a direction of motion.

8. A radiation therapy device according to claim 7, said control unit adapted to store multiple configurations of said imaging panel and automatically move the imaging panel to the stored configuration.

9. A radiation therapy device according to claim 6, further including a controller adapted to define a boundary for a radiation field and determine if an extent of said boundary exceeds an extent of a boundary of an imaging area.

10. A radiation therapy device according to claim 9, said control unit adapted to interface to a gantry control unit and display using said graphical user interface motions of said gantry and said portal imaging device.

11. A method for providing a portal imaging device positioning apparatus attachable to a radiation therapy device gantry, comprising:
    providing a support attachable to said gantry;
    providing a vertically-adjustable portal imaging device positioner attachable to said support, said portal imaging device positioner operable in a first mode and a second mode, wherein in said first mode said portal imaging device positioner maintains an imaging panel in position to receive radiation passing through a body maintained in a patient plane, and wherein in said second mode portal imaging device positioner maintains said imaging panel to receive radiation substantially at said patient plane; and
    providing a graphical user interface adapted to control deployment of said portal imaging device positioner.

12. A method according to claim 11, said graphical user interface adapted to display movements of said portal imaging device positioner and said gantry.

13. A method according to claim 12, further including providing a controller adapted to define a boundary for a radiation field and determine if an extent of said boundary exceeds an extent of a boundary of an imaging area.

14. A method according to claim 11, said graphical user interface adapted to allow a user to adjust a position of the imaging panel using buttons with symbols labeled to indicate a direction of motion.

15. A method according to claim 14, said graphical user interface adapted to store multiple configurations of said imaging panel and automatically move the imaging panel to the stored configuration.

* * * * *